United States Patent [19]

Lee

[11] 4,423,245
[45] Dec. 27, 1983

[54] PROCESS FOR PREPARING 2,5-DICHLORO-3-NITROBENZOIC ACID FROM 2,5-DICHLORO-3-NITRO-P-XYLENE

[75] Inventor: Young-Jin Lee, Raleigh, N.C.

[73] Assignee: Union Carbide Corporation, Danbury, Conn.

[21] Appl. No.: 340,262

[22] Filed: Jan. 18, 1982

[51] Int. Cl.$^3$ .............................................. C07C 51/265
[52] U.S. Cl. .................................................... 562/416
[58] Field of Search ........................................ 562/416

[56] References Cited

U.S. PATENT DOCUMENTS

| | | | |
|---|---|---|---|
| 3,139,452 | 6/1964 | Hay | 562/416 |
| 3,681,446 | 8/1972 | Ledford | 562/416 |
| 3,944,601 | 3/1976 | Kuhlmann | 562/416 |
| 4,007,223 | 2/1977 | Feld | 562/416 |
| 4,088,823 | 5/1978 | Holtz | 562/416 |
| 4,197,412 | 4/1980 | Kimura | 562/416 |
| 4,230,882 | 10/1980 | Seko | 562/416 |
| 4,252,979 | 2/1981 | Jacques | 562/438 |

*Primary Examiner*—Michael L. Shippen
*Attorney, Agent, or Firm*—R. C. Brown; W. E. Dickheiser; W. R. Moran

[57] ABSTRACT

A process for the production of 2,5-dichloro-3-nitrobenzoic acid which comprises reacting 2,5-dichloro-3-nitro-p-xylene in a saturated aliphatic carboxylic acid solvent with oxygen at elevated temperature and pressure in the presence of a catalyst system which comprises a transition metal oxidation catalyst and a bromine promoter.

21 Claims, No Drawings

PROCESS FOR PREPARING 2,5-DICHLORO-3-NITROBENZOIC ACID FROM 2,5-DICHLORO-3-NITRO-P-XYLENE

BACKGROUND OF THE INVENTION

This invention relates to a novel process for the production of 2,5-dichloro-3-nitrobenzoic acid. This compound is an important intermediate in the production of 2,5-dichloro-3-aminobenzoic acid, an important selective herbicide used, for example, in the control of annual broadleaf weeds and annual grasses in soybeans and other crops.

U.S. patent application Ser. No. 133,791, filed on Mar. 25, 1980 discloses a process for the production of 2,5-dichloro-3-nitrobenzoic acid by the nitration of 2,5-dichlorobenzoic acid with mixed nitric and sulfuric acids. U.S. patent application Ser. No. 325569, filed on Nov. 27, 1981, discloses a process for the production of 2,5-dichloro-3-nitrobenzoic acid by the nitration and subsequent oxidative decarboxylation of 2,5-dichloro-p-xylene by treatment with nitric acid.

The present invention involves a one-step liquid phase process for the conversion of 2,5-dichloro-3-nitro-p-xylene into 2,5-dichloro-3-nitrobenzoic acid utilizing a catalyst system comprising of a transition metal oxidation catalyst and a bromine promoter. Most preferably the transition metal oxidation catalyst comprises a cobalt catalyst and a manganese co-catalyst. An initiator or activator may also be employed if so desired.

This novel process provides the economic benefits of a one-step process coupled with the additional safety features which are present when less reactive organic acids such as acetic acid, rather than large amounts of stronger inorganic acids such as nitric acid and sulfuric acid, are employed to accomplish such oxidation and decarboxylation.

DESCRIPTION OF THE INVENTION

The present invention relates to a one-step liquid phase synthesis of 2,5-dichloro-3-nitrobenzoic acid, utilizing 2,5-dichloro-3-nitro-p-xylene as a starting material. The 2,5-dichloro-3-nitro-p-xylene is oxidized by treatment with oxygen at elevated temperature and pressure in the presence of a catalyst, utilizing a saturated aliphatic carboxylic acid as a solvent. The catalyst system employed comprises transition metal oxidation catalyst and a bromine promoter. In addition an activator or initiator may also be present.

The process is postulated to proceed in the following manner:

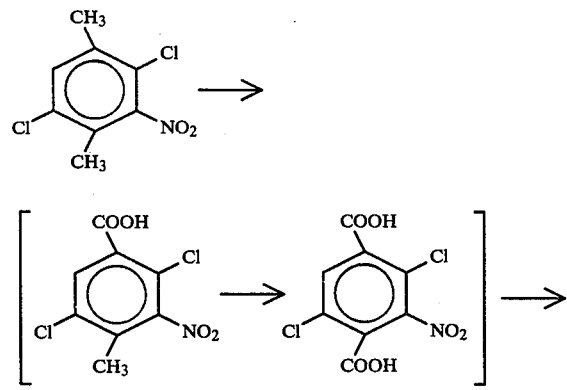

-continued

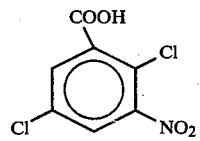

It is believed that the 2,5-dichloro-3-nitro-p-xylene is first partially oxidized to form 2,5-dichloro-3-nitro-p-toluic acid. This first intermediate is then fully oxidized to produce 2,5-dichloro-3-nitro terephtalic acid. The fully oxidized 2,5-dichloro-3-nitroterephtalic acid intermediate decarboxylates readily into 2,5-dichloro-3-nitrobenzoic acid under the reaction conditions employed.

The 2,5-dichloro-3-nitro-p-xylene employed as a starting material may be prepared by the dichlorination and nitration of p-xylene in accordance with methods familiar to one skilled in the art. For example, U.S. Pat. No. 3,035,103 discloses a process for producing 2,5-dichloro-p-xylene by reacting p-xylene with chlorine in the presence of a solvent utilizing a ferric chloride catalyst. Similarly, U.S. Pat. No. 4,166,075 discloses a process for the 2,5-dichlorination of p-xylene utilizing ferric or antimony chloride as a catalyst and an aliphatic, halogenated or unhalogenated co-catalyst having an oxygen function. U.S. Pat. Nos. 3,928,476 and 3,966,830 disclose processes for the nitration of halogenated benzene derivatives, such processes comprising treatment with nitric acid and either (1) an oxacid of sulfur or phosphorus, or (2) silica, alumina or silica-alumina oxide respectively.

Any transition metal oxidation catalyst, including, for example, cobalt, manganese, vanadium, lead, iron, cerium, nickel, copper, chromium, etc., can be utilized in the practice of this invention. The preferred transition metal oxidation catalyst is cobalt. Most preferably, a manganese co-catalyst is also present. The cobalt compound catalysts useful in the process of the instant invention include organic and inorganic cobalt salts such as, for example, cobalt acetate, cobalt naphthenate, cobalt 2-ethylhexanoate, cobalt bromide, cobalt oxide, cobalt hydroxide, cobalt toluate, cobalt oleate, cobalt acetylacetonate, and the like. When acetic acid is employed as the solvent, cobalt acetate is preferred as this salt has a common anion with such solvent and is thus very soluble in the reaction medium. The cobalt salt is preferably employed in an amount of from about 0.05 to about 10 (more preferably from about 0.2 to about 2) weight percent, based on the weight of the carboxylic acid solvent employed.

The manganese co-catalyst compounds which may be employed include organic and inorganic manganese salts such as, for example, manganese acetate, manganese naphthenate, manganese 2-ethylhexanoate, manganese bromide, manganese oxide, manganese hydroxide, manganese toluate, manganese oleate, manganese acetylacetonate and the like. Manganese acetate is the preferred manganese salt. The manganese salt can be present in an amount of from about 0.05 to about 10 weight percent, based on the weight of the acid solvent employed.

The promoter employed in the catalyst system of this invention is a substance affording bromine in elemental, ionic, organic or inorganic form. Exemplary of the bromine compounds which may be employed are hydrobromic acid, sodium bromide, potassium bromide, tetrabromoethane and the like. The bromine may also be present as the anion of the transition metal oxidation catalyst employed. For example, example 4 in Table I below indicates that 47 percent of the reaction product formed was 2,5-dichloro-3-nitro-benzoic acid when cobalt bromide was employed as the transition metal oxidation catalyst and bromine promoter source. Aqueous hydrobromic acid is the preferred bromine compound. The promoter is preferably employed in an amount of from about 0.05 to about 20 weight percent, based on the weight of the carboxylic acid solvent employed.

When cobalt acetate, manganese acetate, and hydrobromic acid are used as the catalyst system the weight ratio of cobalt acetate:manganese acetate:hydrobromic acid is preferably 1:0.2-1.0:1.5.

Other ingredients can also be employed in minor amounts in the instant process, provided they do not adversely affect the production of 2,5-dichloro-3-nitrobenzoic acid. For example, activators such as acetaldehyde, chromium oxide, methyl-ethyl ketone, and nitric acid may be employed. Nitric acid is the preferred activator.

In addition, free radical initiators such as t-butyl-peroxide may be employed to shorten the induction period. The initiator yields free radicals on thermal decomposition and initiates the oxidation. Addition of an initiator may not be necessary when the invention is practiced in a continuous process.

The reaction temperature may range from about 100° C. to about 250° C. Higher temperatures (above 230° C.) may result in degradation of the 2,5-dichloro-3-nitrobenzoic acid product as well as in decomposition of the carboxylic acid solvent. Lower temperatures may cause the reaction to slow to the point where it is no longer practical. Reaction temperatures of from about 190° C. to about 210° C. are preferred.

The reaction may be performed at any pressure sufficient to maintain the liquid phase at the reaction temperature selected. Pressures of from about 100 to about 600 psig may be employed with pressures of from about 250 to about 400 psig preferred.

Although any saturated aliphatic carboxylic acid which is inert to oxidation under the reaction conditions, including propionic acid, butyric acid, etc., may be employed, acetic acid is preferred as the solvent. When acetic acid is utilized preferably from about 10 to about 30 weight percent of 2,5-dichloro-3-nitro-p-xylene, based upon the weight of acetic acid solvent present, should be employed.

Aqueous acetic acid may also be employed as a solvent. The amount of water in the acid medium should not exceed about 20 volume percent, and should preferably be limited to about 10 volume percent.

Gaseous oxygen present as either pure molecular oxygen, air or an oxygen containing gas is used as the oxidant. The ratio of oxygen to 2,5-dichloro-3-nitro-p-xylene should be high enough so that the reaction mixture is not oxygen starved. However, care should be taken so that such ratio is not too high so as to avoid the creation of an unnecessary safety hazard resulting from an explosive mixture of oxygen, acid and hydrocarbon. For safety reasons, the oxygen concentration in the off-gas should not exceed 8 weight percent.

Reaction time is not critical and is important only to the extent that an optimum amount of 2,5-dichloro-3-nitrobenzoic acid is produced. The reaction time can vary from less than several hours to a day or more depending upon temperature, pressure, etc. The reaction can be monitored by known means, such as gas chromatography, to determine how far the reaction has proceeded.

The reaction type is not critical and any reactor giving good gas-liquid contact in a well mixed liquid is suitable. Mixing may be accomplished by mechanical means or by properly designed gas-spargers. It is preferred that a glass, porcelain, titanium- or tantalum-lined reactor be employed since these materials will minimize any problems associated with the corrosive nature of the hot reaction mixture employed.

The process of the present invention can be conducted in batch, semi-batch or continuous fashion, as may be required to suit a particular commercial purpose.

The following examples are specific illustrations of the practice of this invention.

A series of experiments were conducted under various conditions according to the following general procedure:

A mixture of 2,5-dichloro-3-nitro-p-xylene, catalysts, promoter (and/or activator) and initiator in acetic acid was placed in a 2-liter tantalum autoclave. The reactor was pressurized to the desired pressure with oxygen. The reactor was then slowly heated to an operating temperature with rocking and held there for a predetermined time. The autoclave was cooled to room temperature by blowing cold air on it and then depressurized by venting gas slowly. The preferred method of isolating the product was to dissolve the reaction mixture in acetone. Removal of acetone and solvent by distillation gave the product, including catalysts. The catalysts were removed by washing the product with water twice. The product was analyzed by gas chromatography as a dimethyl derivative. The results obtained are summarized in Table 1.

TABLE I

Oxidation of 2,5-Dichloro-3-nitro-p-xylene

| Example | DCNX (g) | AcOH (ml) | CO(OAc)$_2$ 4H$_2$O (g) | Mn(OAc)$_2$ 4H$_2$O (g) | HBr 48% (g) | Other Catalysts or Activator | t-Butyl Peroxide (g) | Temp (°C.) | Oxygen Pressure (psig) | Reaction Time (hr) | Product (g) | Product Composition DNB:DCNTA: Others |
|---|---|---|---|---|---|---|---|---|---|---|---|---|
| 1 | 22 | 100 | 1.0 | 0.5 | 1.4 | | 0.5 | 200 | 300 | 17 | 8.9 | 69:24:7 |
| 2 | 22 | 100 | 1.0 | 0.5 | 1.4 | | 0.5 | 180 | 300 | 18 | 20.2 | Mostly DCNTA |
| 3 | 22 | 100 | 0.5 | 0.3 | 0.7 | | 0.5 | 200 | 400 | 16.5 | 19 | 43:47:10 |
| 4 | 33 | 100 | — | — | — | CoBr$_2$.6H$_2$O (0.5g) | 0.5 | 200 | 300 | 19.5 | 22.1 | 47:36:17 |
| 5 | 33 | 100 | 0.5 | 0.3 | 0.7 | | 0.5 | 200 | 300 | 42 | 23.0 | 59:24:17 |
| 6 | 33 | 90 | 0.5 | 0.3 | 0.7 | HNO$_3$(10 ml) | 0.5 | 200 | 300 | 15 | 18.0 | 78:8:14 |
| 7 | 22 | 50 | 0.5 | 0.3 | 0.7 | CH$_3$CHO(0.5-g) | 0.5 | 200 | 300 | 18.5 | 18.2 | 46:36:18 |
| 8 | 22 | 50 | 0.5 | 0.3 | 0.7 | Cr$_2$O$_3$(0.5g) | 0.5 | 200 | 300 | 20 | 15.1 | 57:18:25 |

TABLE I-continued

| | | | | | | Oxidation of 2,5-Dichloro-3-nitro-p-xylene | | | | | |
|---|---|---|---|---|---|---|---|---|---|---|---|
| Example | DCNX (g) | AcOH (ml) | CO(OAc)$_2$ 4H$_2$O(g) | Mn(OAc)$_2$ 4H$_2$O(g) | HBr 48% (g) | Other Catalysts or Activator | t-Butyl Peroxide (g) | Temp (°C.) | Oxygen Pressure (psig) | Reaction Time (hr) | Product (g) | Product Composition DNB:DCNTA: Others |
| 9 | 22 | 50 | 0.5 | 0.3 | 0.7 | CH$_3$CHO(5.0-g) CH$_3$CHO(5g) | 0.5 | 200 | 500 | 18 | 15.3 | 58:14:28 |

DCNX - 2,5-dichloro-3-nitro-p-xylene
DNB - 2,5-dichloro-3-nitrobenzoic acid
AcOH - acetic acid
Co(OAc)$_2$4H$_2$O - cobalt acetate
Mn(OAc)$_2$4H$_2$O - manganese acetate
DCNTA - 2,5-dichloro-3-nitro-p-toluic acid The data in Table I indicates that a reaction product which contains up to 78 percent 2,5-dichloro-3-nitrobenzoic acid can be realized by treatment of 2,5-dichloro-3-nitro-p-xylene in accordance with the novel process disclosed herein. Although satisfactory results are obtained in the absence of an activator, the data indicates that a significant improvement is achieved when a relatively small amount of nitric acid is present in the reaction mixture as an activator.

I claim:

1. A process for the preparation of 2,5-dichloro-3-nitrobenzoic acid which comprises reacting 2,5-dichloro-3-nitro-p-xylene in a saturated aliphatic carboxylic acid solvent with oxygen in the presence of a catalyst system, wherein such catalyst system comprises:
   (a) a transition metal oxidation catalyst; and
   (b) a bromine promoter.

2. The process of claim 1 wherein the transition metal oxidation catalyst is one of cobalt, manganese, vanadium, lead, iron, cerium, nickel, copper, chromium or a mixture thereof.

3. The process of claim 1 wherein the saturated aliphatic carboxylic acid solvent is one of acetic acid, propionic acid, butyric acid and mixtures thereof.

4. The process of claim 1 wherein the reaction is conducted at a temperature of from about 100° C. to about 250° C.

5. The process of claim 4 wherein the reaction is conducted at a temperature of from about 190° C. to about 210° C.

6. The process of claim 1 wherein the reaction is conducted at a pressure of from about 100 to about 600 psig.

7. The process of claim 6 wherein the reaction is conducted at a pressure of from about 250 to about 400 psig.

8. A process for the preparation of 2,5-dichloro-3-nitrobenzoic acid which comprises reacting 2,5-dichloro-3-nitro-p-xylene in a saturated aliphatic carboxylic acid solvent with oxygen in the presence of a catalyst system, wherein such catalyst system comprises:
   (a) a cobalt oxidation catalyst;
   (b) a manganese co-catalyst; and
   (c) a bromine promoter.

9. The process of claim 8 wherein the cobalt catalyst is one of cobalt acetate, cobalt naphthenate, cobalt 2-ethylhexanoate, cobalt bromide, cobalt oxide, cobalt hydroxide, cobalt toluate, cobalt oleate, cobalt acetylacetonate and mixtures thereof.

10. The process of claim 8 wherein the manganese co-catalyst is one of manganese acetate, manganese naphthenate, manganese 2-ethyl-hexanoate, manganese bromide, manganese hydroxide, manganese toluate, manganese oleate, manganese acetyl-acetonate and mixtures thereof.

11. The process of claim 8 wherein the bromine promoter is aqueous hydrobromic acid.

12. The process of claim 8 wherein the reaction mixture contains t-butyl peroxide as an initiator.

13. The process of claim 8 wherein the reaction contains an activator selected from the group acetaldehyde, chromium oxide, methyl ethyl ketone and nitric acid.

14. The process of claim 13 wherein the activator is nitric acid.

15. The process of claim 8 wherein the reaction is conducted at a temperature of from about 100° C. to about 250° C.

16. The process of claim 15 wherein the reaction is conducted at a temperature of from about 190° C. to about 210° C. is employed.

17. The process of claim 8 wherein the reaction is conducted at a pressure of from about 100 to about 600 psig.

18. The process of claim 17 wherein the reaction is conducted at a pressure of from about 250 to about 400 psig.

19. The process of claim 8 wherein the saturated aliphatic carboxylic acid solvent is one of acetic acid, propionic acid, butyric acid and mixtures thereof.

20. A process for the preparation of 2,5-dichloro-3-nitrobenzoic acid which comprises reacting 2,5-dichloro-3-nitro-p-xylene in an acetic acid solvent with oxygen at a temperature of from about 190° C. to about 210° C. and a pressure of from about 250 to about 400 psig in the presence of a catalyst system, wherein such catalyst system comprises:
   (a) cobalt acetate;
   (b) manganese acetate;
   (c) aqueous hydrobromic acid;
   (d) tert-butyl peroxide, and
   (e) nitric acid.

21. The process of claim 20 wherein the cobalt acetate, manganese acetate and aqueous hydrobromic acid have a weight ratio of 1:0.2-1.0:1.5.

* * * * *